(12) United States Patent
Sevimli et al.

(10) Patent No.: US 11,642,184 B2
(45) Date of Patent: May 9, 2023

(54) UNIVERSAL SURGICAL TOOL EXCHANGE AND IDENTIFICATION SYSTEM

(71) Applicant: THE JOHNS HOPKINS UNIVERSITY, Baltimore, MD (US)

(72) Inventors: Yunuscan Sevimli, Baltimore, MD (US); Russell H. Taylor, Severna Park, MD (US)

(*) Notice: Subject to any disclaimer, the term of this patent is extended or adjusted under 35 U.S.C. 154(b) by 465 days.

(21) Appl. No.: 16/625,944

(22) PCT Filed: Jun. 27, 2018

(86) PCT No.: PCT/US2018/039693
§ 371 (c)(1),
(2) Date: Dec. 23, 2019

(87) PCT Pub. No.: WO2019/005921
PCT Pub. Date: Jan. 3, 2019

(65) Prior Publication Data
US 2020/0155244 A1    May 21, 2020

Related U.S. Application Data

(60) Provisional application No. 62/525,265, filed on Jun. 27, 2017.

(51) Int. Cl.
*A61B 34/30* (2016.01)
*A61B 90/98* (2016.01)

(52) U.S. Cl.
CPC .............. *A61B 34/30* (2016.02); *A61B 90/98* (2016.02)

(58) Field of Classification Search
CPC ............... A61B 34/30–77; A61B 90/98; F16B 2/18–185; F16B 2200/30; F16B 5/0052
See application file for complete search history.

(56) References Cited

U.S. PATENT DOCUMENTS

| | | | | |
|---|---|---|---|---|
| 3,082,555 A | * | 3/1963 | Hill | E02F 9/28 37/453 |
| 3,090,086 A | * | 5/1963 | Fata | B27F 1/00 403/381 |
| 4,019,298 A | * | 4/1977 | Johnson, IV | E04B 1/54 403/381 |
| 4,058,173 A | * | 11/1977 | Carson | E02F 3/815 172/753 |

(Continued)

*Primary Examiner* — Tan-Uyen T Ho
*Assistant Examiner* — Charles M Wei (57) ABSTRACT

The present invention is directed to a device for allowing universal surgical tool exchange. The device of the present invention includes a tool-side adapter and a robot-side adapter that combine the benefits of a robot in the operating room (OR) with a system that has minimal impact on the current surgical workflow. The device of the present invention allows surgeons to preserve their natural grip on the surgical tool, creates a reliable and repeatable connection between the tool and the robot, and allows the user to rapidly swap the tools in and out from the surgical robot using a single-handed motion. A unique RFID tag and receiver is embedded in the tool-side adapter and the robot-side adapter, respectively to allow the robot to identify the tool that has been engaged. The present invention is universally applicable to any robotic system that is intended to hold a set of hand instruments.

19 Claims, 5 Drawing Sheets

(56) References Cited

U.S. PATENT DOCUMENTS

| | | | | |
|---|---|---|---|---|
| 4,175,884 A * | 11/1979 | Cheng | F16B 12/125 | 248/188 |
| 4,971,474 A * | 11/1990 | Sprague | B64G 1/641 | 403/381 |
| 5,015,518 A * | 5/1991 | Sasaki | H05B 7/14 | 428/56 |
| 5,244,300 A * | 9/1993 | Perreira | E04B 1/2403 | 403/333 |
| 5,433,518 A * | 7/1995 | Skov | A47B 88/9414 | 312/348.1 |
| 5,478,145 A * | 12/1995 | Kamachi | F16B 5/02 | 211/187 |
| 6,176,641 B1 * | 1/2001 | Schenk | F16M 11/041 | 403/374.5 |
| 6,216,410 B1 * | 4/2001 | Haberman | E04F 13/12 | 52/592.1 |
| 2003/0175075 A1 * | 9/2003 | Garrison | B23Q 16/08 | 403/381 |
| 2005/0283137 A1 * | 12/2005 | Doyle | A61B 50/30 | 606/1 |
| 2006/0165482 A1 * | 7/2006 | Olberding | E04B 1/24 | 403/381 |
| 2006/0233605 A1 * | 10/2006 | Vendetti | F41G 11/003 | 403/381 |
| 2008/0249551 A1 * | 10/2008 | Sunaoshi | A61B 90/90 | 606/170 |
| 2008/0262654 A1 * | 10/2008 | Omori | A61B 34/72 | 901/30 |
| 2011/0288573 A1 * | 11/2011 | Yates | A61B 90/98 | 227/175.1 |
| 2012/0298719 A1 * | 11/2012 | Shelton, IV | A61B 17/105 | 227/176.1 |
| 2013/0110129 A1 * | 5/2013 | Reid | A61B 34/37 | 403/326 |
| 2014/0066944 A1 * | 3/2014 | Taylor | A61B 34/32 | 606/103 |
| 2016/0235490 A1 * | 8/2016 | Srivastava | A61B 34/30 | |
| 2017/0086831 A1 * | 3/2017 | Shelton, IV | A61B 34/71 | |
| 2017/0156803 A1 * | 6/2017 | McGrogan | A61B 34/70 | |
| 2018/0168746 A1 * | 6/2018 | Swayze | A61B 17/3423 | |
| 2020/0405296 A1 * | 12/2020 | Shelton, IV | A61B 17/07207 | |

* cited by examiner

UNIVERSAL SURGICAL TOOL EXCHANGE AND IDENTIFICATION SYSTEM

CROSS-REFERENCE TO RELATED APPLICATIONS

This application is a 35 U.S.C. § 371 U.S. national entry of International Application PCT/US2018/039693, having an international filing date of Jun. 27, 2018, which claims the benefit of U.S. Provisional Application No. 62/525,265, filed Jun. 27, 2017, the content of each of the aforementioned applications is herein incorporated by reference in their entirety.

FIELD OF THE INVENTION

The present invention relates generally to surgical instruments. More particularly, the present invention relates to a universal surgical tool exchange and identification system.

BACKGROUND OF THE INVENTION

During conventional, non-robotic surgery, surgeons are accustomed to having a reliable grip on a hand tool if it is being used. Additionally, surgeons during a conventional surgery are able to rapidly change tools when needed either alone or with the help of an operating room (OR) assistant. With robotic assisted surgery, there is often limited ability to grip the tool or exchange tools quickly and easily. Introduction of a robotic system that uses the same conventional tools into the OR has many potential benefits to patient outcome, surgeon comfort and duration of surgery, depending on the capabilities of the system. However, such a system may also disturb the conventional workflow, thus limiting the adoption of the system.

Accordingly, there is a need in the art for a universal surgical tool exchange and identification system to ease work-flow.

SUMMARY OF THE INVENTION

The foregoing needs are met, to a great extent, by the present invention which provides a device for securing a tool to a robot includes a tool-side adapter having a radio-frequency identification (RFID) transmitter. The device includes a robot-side adapter comprising a coupling for mounting the robot-side adapter to an end effector of the robot. The robot-side adapter also includes an RFID receiver. A geometry of the tool-side adapter and of the robot-side adapter are configured to couple together to hold the tool at an end effector of the robot. The device also includes a locking mechanism to secure the tool-side adapter to the robot-side adapter.

In accordance with an aspect of the present invention, the device includes a tool holder coupled to the tool-side adapter. The tool holder includes custom features to match the shape and function of the individual tool to be secured to the robot. The tool-side adapter includes a coupling for mounting the tool holder to the tool-side adapter. The tool holder is configured to be positioned on the tool such that a surgeon's natural grip on the tool is preserved. The RFID transmitter transmits a number unique to the tool. The geometry of the tool-side adapter includes a male connector. The geometry of the robot-side adapter takes the form of a female connector. The tool-side adapter and the robot-side adapter take the form of a dovetail-type connector. The robot-side adapter takes the form of a vertically aligned dovetail groove. The tool-side adapter includes a vertically aligned dovetail protrusion. The vertically aligned dovetail groove of the robot-side adapter tapers from larger at a top to smaller at a bottom to ensure that the tool is held securely by the robot. The vertically aligned dovetail protrusion of the tool-side adapter is tapered to match the shape of the vertically aligned dovetail grove of the robot-side adapter. The locking mechanism includes a spring-loaded locking mechanism.

In accordance with another aspect of the present invention, the robot-side adapter includes a pin and the tool-side adapter includes a hole, wherein the pin is configured to engage with the hole to keep the robot-side adapter and the tool-side adapter coupled during use. The pin is spring loaded and includes a torsional spring. The pin is biased to an engaged position and is disengaged by applying a force against the torsional spring. The device includes a thumb operated lever for disengaging the pin. The RFID receiver reads the RFID transmitter whenever the tool-side adapter is coupled to the robot-side adapter. The device includes a receiver for receiving the tool information from the RFID receiver.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a device for allowing universal surgical tool exchange. The device of the present invention includes a tool-side adapter and a robot-side adapter that combine the potential benefits of utilizing a robot in the operating room (OR) with a system that has minimal impact on the surgical workflow that surgeons are accustomed to in the OR. The device of the present invention allows surgeons to preserve their natural grip on the surgical tool, creates a reliable and repeatable connection between the tool and the robot, and allows the user to rapidly swap the tools in and out from the surgical robot using a single-handed motion. A unique RFID tag and receiver is embedded in the tool-side adapter and the robot-side adapter, respectively to allow the robot to identify the tool that has been engaged. The present invention is universally applicable to any robotic system that is intended to hold a set of hand instruments.

The present invention takes the form of a mechanical system to attach most surgical hand tools to the end-effector of a robotic system. During conventional (non-robotic) surgery, surgeons are accustomed to having a reliable grip on the hand tool and being able to rapidly swap the tools with another one when needed by the help of an OR assistant. Introduction of a robotic system that uses the same conventional tools into the OR has many potential benefits to patient outcome, surgeon comfort and duration of surgery depending on the capabilities of the system, but may severely disturb the conventional workflow, thus limiting the adoption of the system. The Universal Surgical Tool Exchanger combines the potential benefits of utilizing a robot in the OR with a system that has minimal impact on the surgical workflow that surgeons are accustomed to. The invention allows surgeons to preserve their natural grip on the surgical tool, creates a reliable and repeatable connection between the tool and the robot, and allows the user to rapidly swap the tools in and out using a single-handed motion. The unique radio-frequency identification (RFID) tag and receiver embedded in the tool and the robot side, respectively, allow the robot to identify the tool it is holding on to. The invention is universally applicable to any robotic system that is intended to hold a set of hand instruments.

Figure 1A:
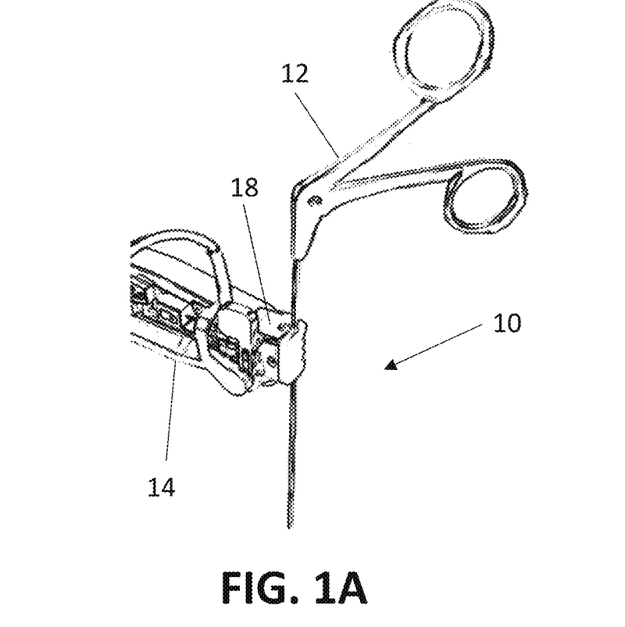
FIG. 1A illustrates a surgical instrument attached to a surgical robot, using the device of the present invention.
Figure 1B:
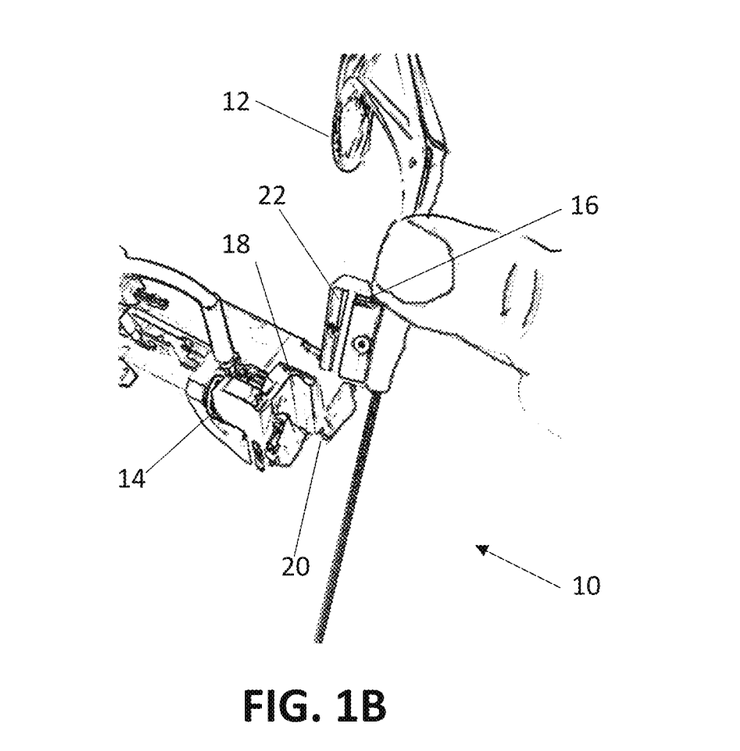
FIG. 1B illustrates a surgical instrument with an adapter according to an embodiment of the present invention in position to be attached to a surgical robot equipped with a second adapter according to an embodiment of the present invention.
Figure 2A:
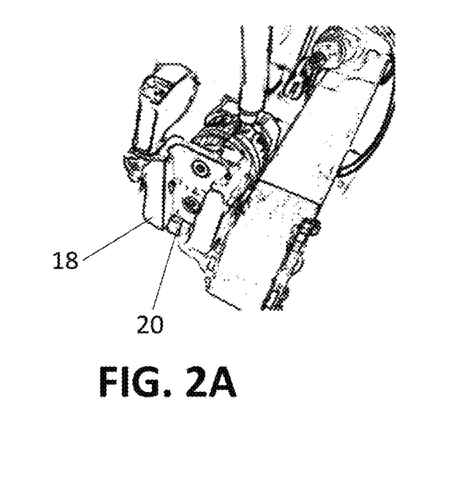
FIGS. 2A-2D illustrate perspective views of a surgical robot-side adapter, according to an embodiment of the present invention.
Figure 2B:
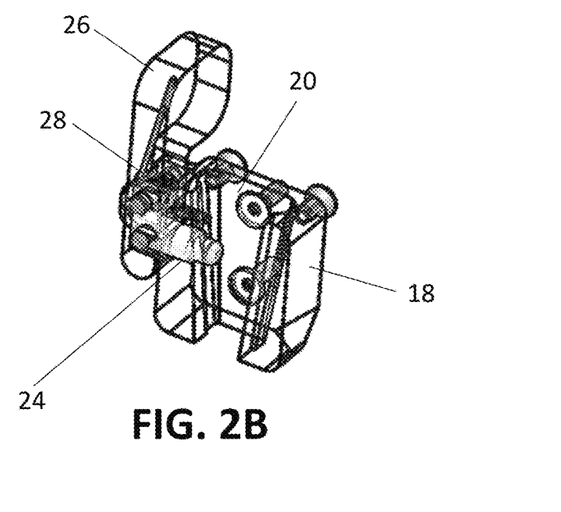
Figure 2C:
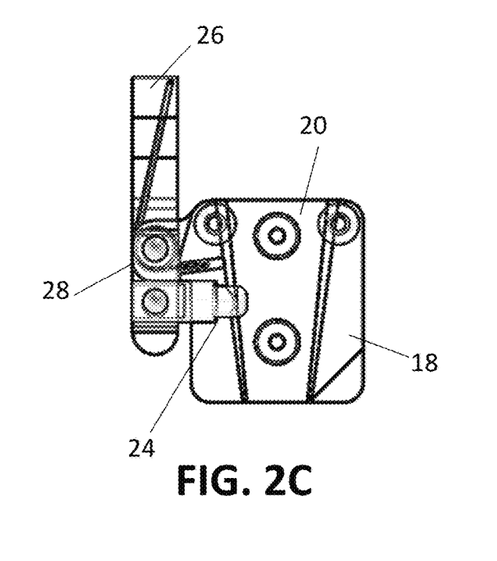
Figure 2D:
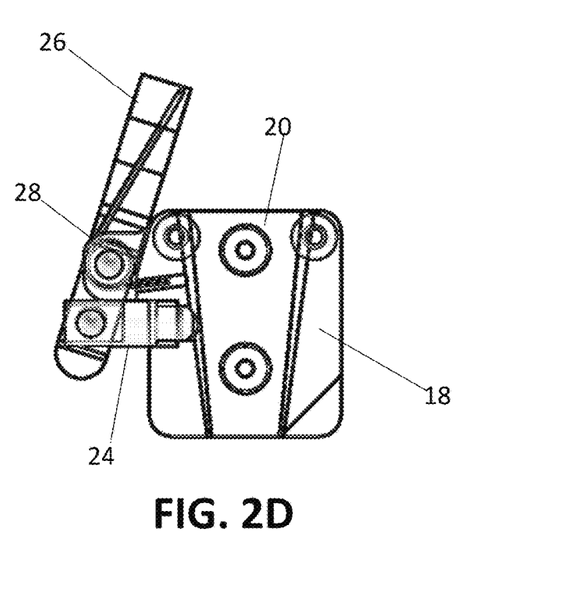
Figures 3A, 3B, 3C:
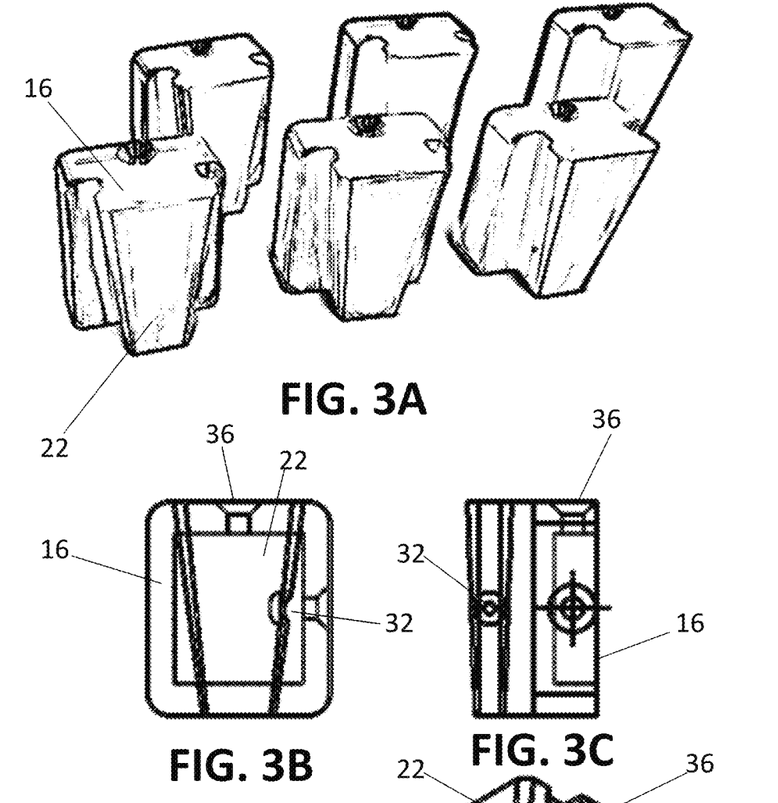
FIGS. 3A-3E illustrate perspective views of a surgical tool-side adapter, according to an embodiment of the present invention.
Figures 3D, 3E:
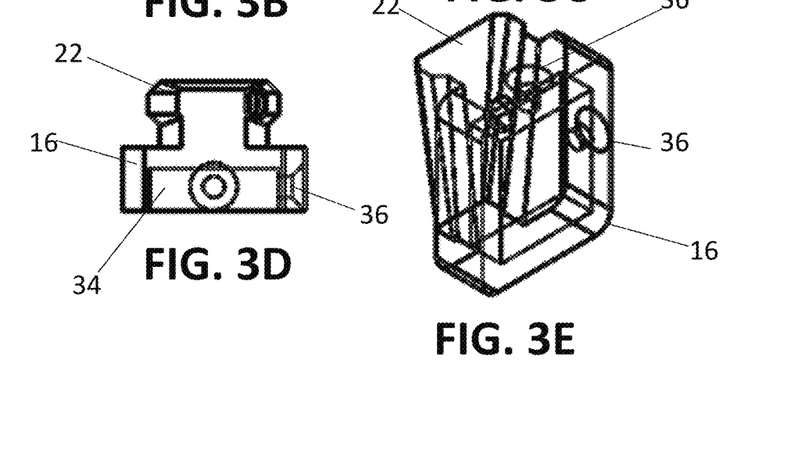

FIG. 1A illustrates a surgical instrument attached to a surgical robot, using the device of the present invention. FIG. 1B illustrates a surgical instrument with an adapter according to an embodiment of the present invention in position to be attached to a surgical robot equipped with a second adapter according to an embodiment of the present invention. As illustrated in FIGS. 1A and 1B, a device 10 according to an embodiment of the present invention couples the surgical tool 12 to the surgical robot 14. The device 10 includes a surgical tool-side adapter 16 and a surgical robot-side adapter 18. The surgical tool-side adapter 16 and the surgical robot-side adapter 18 are configured to couple together quickly and easily, so as to not detract from the workflow in the operating room (OR). Further, with respect to FIG. 1B, the device 10 includes a dovetail-type coupling with the surgical robot-side adapter 18 including a dovetail 20 that receives a correspondingly shaped pin 22 of the surgical tool-side adapter 16. While a dovetail-type coupling is described as an example herein, any suitable coupling known to or conceivable by one of skill in the art could also be used.

FIGS. 2A-2D illustrate perspective views of a surgical robot-side adapter, according to an embodiment of the present invention. As illustrated in FIGS. 2A-2D, the surgical robot-side adapter 18 includes a female connector 20. The robot-side adapter 18 attaches onto an end-effector of the robot. In the preferred embodiment shown herein the female connector takes the form of a vertically aligned dovetail groove to match the tool-side adapter when engaged. As noted above, this is included merely by way of example, and any shape or style of coupling know to or conceivable by one of skill in the art could be used. The female connector 20 tapers from larger at the top to smaller at the bottom, to ensure that the tool coupled with the robot is held securely. In order to hold the two sides together, the robot-side adapter features a spring loaded locking pin 24 that slides horizontally and engages with a corresponding notch on the tool-side adapter. The spring loaded locking pin 24 is actuated by a lever 26. The spring loaded locking pin 24 is engaged in default position but can be disengaged by applying a force against a torsional spring 28 through a thumb operated lever. This arrangement allows the two sides to be easily disengaged by a single handed motion. The locking pin is engaged in FIG. 2C and the locking pin is disengaged in FIG. 2D.

FIGS. 3A-3E illustrate perspective views of a surgical tool-side adapter, according to an embodiment of the present invention. As illustrated in FIGS. 3A-3E, the surgical tool-side adapter 16 includes a male connector 22. The tool-side adapter 16 is a passive component that features a vertically aligned dovetail protrusion configured to match the robot-side adapter for a secure engagement. On the side of the dovetail protrusion, a blind hole 32 aligns with the locking pin of the robot-side adapter and acts as the keyhole to keep the two components together. In some embodiments, on the opposite side of the dovetail protrusion from the blind hole 32, the tool-side adapter 16 features a standardized rectangular connection port 34 and screw holes 36 to provide the attachment point to the custom tool holder described further herein.

Figure 4:
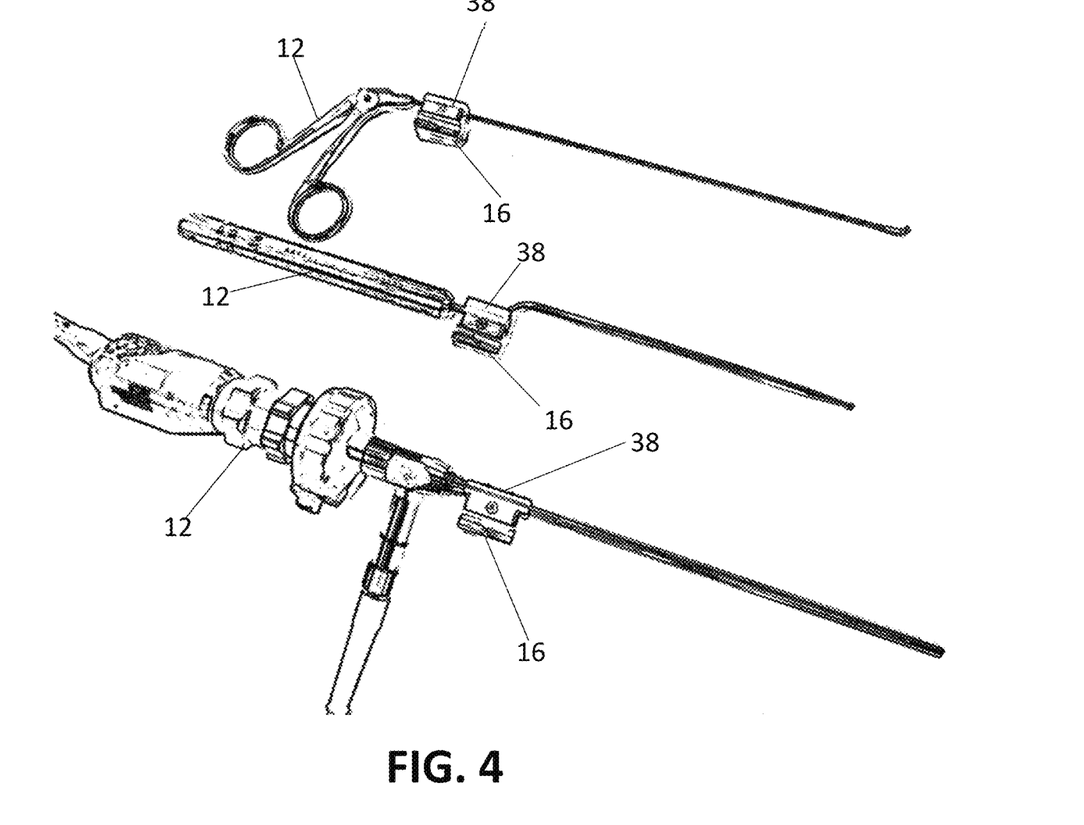
FIG. 4 illustrates a custom tool holder, according to an embodiment of the present invention.

FIG. 4 illustrates a custom tool holder, according to an embodiment of the present invention. As illustrated in FIG. 4, the custom tool holder 38 is a component that attaches the standard surgical hand tool 12 to the tool-side adapter 16. The size and shape of the tool holder 38 depends on the surgical tool to be held. Depending on the function of the tool, the holder 38 can grip the tool either rigidly or can be made to preserve the rotation of the tool along its axis. The side of the holder 38 away from the tool features the standardized connection port that mates with the tool-side adapter and is fixed in place to the tool by screws.

Figure 5:
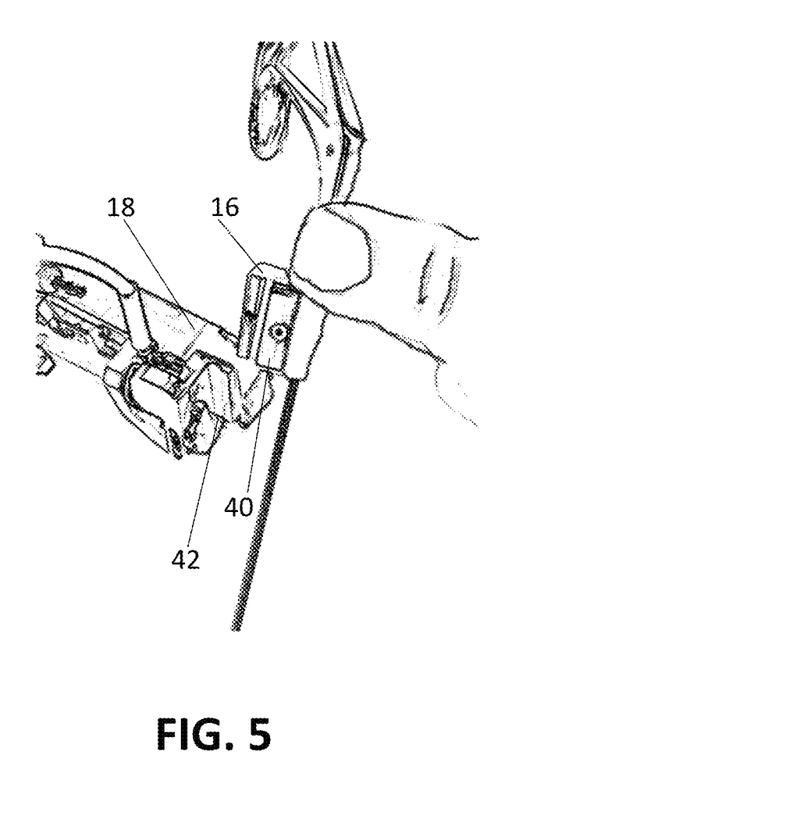
FIG. 5 illustrates a tool identifying tag, according to an embodiment of the present invention.

FIG. 5 illustrates a tool identifying tag, according to an embodiment of the present invention. In certain cases it may be necessary for the robot to "know" the attached tool in order to achieve the following: compensate for the weight of a tool; enforce a remote center of rotation about a point along the shaft of the tool; enforce virtual fixtures with respect to the tool tip; and supply power to an electric tool. To address this need, each surgical tool-side adapter 16 has an RFID tag 40 with a unique ID. A RFID receiver 42 is embedded in the female robot-side adapter 18. The RFID receiver 42 reads this tag 40 whenever a tool is placed on the holder. This information is transferred to the robot controller in order to trigger function specific to that tool. Information can be transmitted between the RFID receiver and the surgical robot using wireless or wired communication. The surgical robot can include a receiver for receiving information from the RFID receiver. The surgical robot can process this information with a non-transitory computer readable medium to trigger function specific to the tool engaged in the holder. The non-transitory computer readable medium can be executed by any suitable computing device. The computing device can be specific to the receiver or can be incorporated into the operation console of the surgical robot.

In an exemplary implementation for otolaryngeal surgery, a surgical robot is configured to accommodate most otolaryngeal tools as a result of being equipped with the device of the present invention. This allows the surgeons to use the robot with the tools they are accustomed to. The robot-side adapter includes a female dovetail joint with a spring loaded locking pin. The tool-side adapter is a simple two-sided part: one end is a standard male dovetail joint and the other end is a custom attachment for surgical tools with different shaft diameters. Any tool containing this attachment can simply slide into the robot-side adapter and passively lock into the standard female joint. The tool can then be removed with a single-handed operation by pressing in the lever to disengage the locking pin with the thumb and by sliding the tool out of the holder.

In an experimental implementation, in order to test the ease of use and the ergonomics of the mechanism, 5 subjects with no prior training were asked to swap 3 tools successively using the device of the present invention. After one training round, each subject was given 2 trials and the times for completion were recorded. Each subject was able to swap 3 tools under 5 seconds in total. The average time to put in and take out a tool was under 2 seconds. A previous method for tool switching required manipulation of a thumb-screw and took about three times as long to accomplish a tool swap using both hands.

The RFID recognition function of the present invention can be carried out using a computer, non-transitory computer readable medium, or alternately a computing device or non-transitory computer readable medium incorporated into the robotic device.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The operating console for the device is a non-generic computer specifically designed by the manufacturer. It is not a standard business or personal computer that can be purchased at a local store. Additionally, the console computer can carry out communications with the surgical through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention. While exemplary embodiments are provided herein, these examples are not meant to be considered limiting. The examples are provided merely as a way to illustrate the present invention. Any suitable implementation of the present invention known to or conceivable by one of skill in the art could also be used.

What is claimed is:

1. A device for securing a tool to a robot comprising:
a tool-side adapter comprising a radio-frequency identification (RFID) transmitter;
a robot-side adapter comprising a coupling for mounting the robot-side adapter to an end effector of the robot and the robot-side adapter comprising an RFID receiver,
wherein a geometry of the tool-side adapter and a geometry of the robot-side adapter are configured to couple together to hold the tool at an end effector of the robot and wherein the tool-side adapter and the robot-side adapter comprise a dovetail-type connector; and
a locking mechanism to secure the tool-side adapter to the robot-side adapter.

2. The device of claim 1 further comprising a tool holder coupled to the tool-side adapter.

3. The device of claim 2 wherein the tool holder comprises features to match a shape and a function of the individual tool, such that the individual tool can be secured to the robot.

4. The device of claim 2 wherein the tool-side adapter comprises a coupling for mounting the tool holder to the tool-side adapter.

5. The device of claim 2 wherein the tool holder is configured to be positioned on the tool such that a surgeon's natural grip on the tool is preserved.

6. The device of claim 1 wherein the RFID transmitter transmits a number unique to the tool.

7. The device of claim 1 wherein the geometry of the tool-side adapter comprises a male connector.

8. The device of claim 1 wherein the geometry of the robot-side adapter comprises a female connector.

9. The device of claim 1 wherein the robot-side adapter comprises a vertically aligned dovetail groove.

10. The device of claim 9 wherein the tool-side adapter comprises a vertically aligned dovetail protrusion.

11. The device of claim 10 wherein the vertically aligned dovetail groove of the robot-side adapter tapers from larger at a top to smaller at a bottom to ensure that the tool is held securely by the robot.

12. The device of claim 11 wherein the vertically aligned dovetail protrusion of the tool-side adapter is tapered to match the shape of the vertically aligned dovetail groove of the robot-side adapter.

13. The device of claim 1 wherein the locking mechanism comprises a spring-loaded locking mechanism.

14. The device of claim 1 wherein the robot-side adapter includes a pin and the tool-side adapter includes a hole, wherein the pin is configured to engage with the hole to keep the robot-side adapter and the tool-side adapter coupled during use.

15. The device of claim 14 wherein the tool-side adapter comprises a torsional spring.

16. The device of claim 15 wherein the pin is biased to an engaged position and is disengaged by applying a force against the torsional spring.

17. The device of claim 16 further comprising a thumb operated lever for disengaging the pin.

18. The device of claim 1 wherein the RFID receiver reads the RFID transmitter whenever the tool-side adapter is coupled to the robot-side adapter.

19. The device of claim 1 further comprising a receiver for receiving the tool information from the RFID receiver.

* * * * *